United States Patent [19]

Stähle et al.

[11] 4,277,487
[45] Jul. 7, 1981

[54] SUBSTITUTED 2-PHENYLAMINO-2-IMIDAZOLINES AS BRADYCARDIACS

[75] Inventors: Helmut Stähle; Herbert Köppe; Werner Kummer, all of Ingelheim am Rhein, Fed. Rep. of Germany; Walter Kobinger, Vienna, Austria; Christian Lillie, Vienna, Austria; Ludwig Pichler, Vienna, Austria

[73] Assignee: Boehringer Ingelheim GmbH, Ingelheim am Rhein, Fed. Rep. of Germany

[21] Appl. No.: 58,165

[22] Filed: Jul. 17, 1979

[30] Foreign Application Priority Data

Jul. 19, 1978 [DE] Fed. Rep. of Germany ....... 2831671

[51] Int. Cl.³ .................. A61K 31/415; C07D 233/50
[52] U.S. Cl. .................. 424/273 R; 542/423; 548/315; 548/351; 564/105; 564/238; 564/244
[58] Field of Search .................. 548/351; 542/423; 424/273 R

[56] References Cited

U.S. PATENT DOCUMENTS

| 3,708,485 | 1/1973 | Stähle et al. | 548/351 X |
| 3,850,926 | 11/1974 | Stämle et al. | 548/348 X |

FOREIGN PATENT DOCUMENTS

2102733 8/1972 Fed. Rep. of Germany ........... 548/348

OTHER PUBLICATIONS

*Chemical Abstracts,* 81:62628d (1974), [German Ols 2,259,160, 6/6/74].

*Primary Examiner*—Richard A. Schwartz
*Attorney, Agent, or Firm*—Hammond & Littell, Weissenberger & Muserlian

[57] ABSTRACT

Compounds of the formula

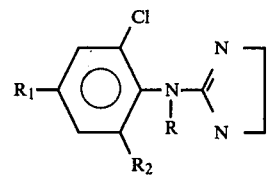

wherein
$R_1$ and $R_2$, which may be the same or different, represent a hydrogen atom, a chlorine atom, or a methyl group, with the proviso that not both $R_1$ and $R_2$ are hydrogen, and
R represents a radical selected from the group consisting of —(CH$_2$)$_2$ —C(CH$_3$)=CH$_2$, —(CH$_2$)$_2$—CH=CH$_2$, —O—CH$_2$—CH=CH$_2$, —O—(CH$_2$)$_2$—CH=CH$_2$, —O—CH$_2$—C(CH$_3$)=CH$_2$, —O=CH$_2$—CH=CH—CH$_3$,

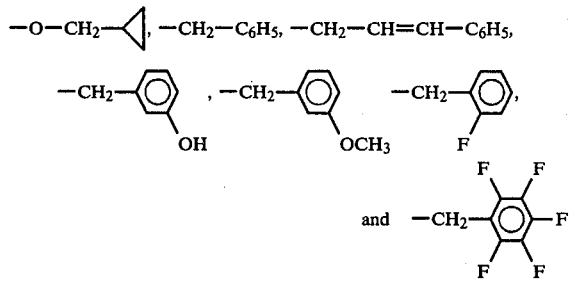

and non-toxic, pharmacologically acceptable acid addition salts thereof. The compounds as well as their salts are useful as bradycardiacs.

3 Claims, No Drawings

SUBSTITUTED 2-PHENYLAMINO-2-IMIDAZOLINES AS BRADYCARDIACS

This invention relates to novel substituted 2-phenylamino-2-imidazolines and non-toxic acid addition salts thereof, to various methods of preparing these compounds, to pharmaceutical compositions containing them as active ingredients, and to methods of using them as bradycardiacs.

More particularly, the present invention relates to a novel class of 2-phenylamino-2-imidazolines represented by the formula

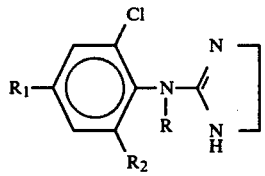
(I)

wherein $R_1$ and $R_2$, which may be the same or different, represent a hydrogen atom, a chlorine atom, or a methyl group, with the proviso that not both $R_1$ and $R_2$ are hydrogen, and R represents a radical selected from the group consisting of $-(CH_2)_2-C(CH_3)=CH_2$, $-(CH_2)_2-CH=CH_2$, $-O-CH_2-CH=CH_2$, $-O-(CH_2)_2-CH=CH_2$, $-O-CH_2-C(CH_3)=CH_2$, $-O-CH_2-CH=CH-CH_3$,

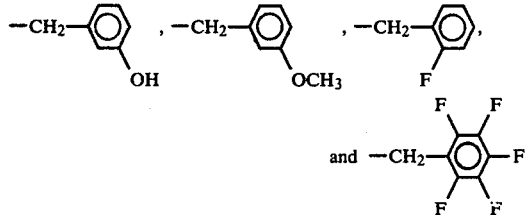

and 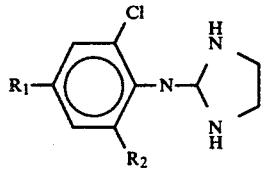

and non-toxic, pharmacologically acceptable acid addition salts thereof.

The compounds of Formula I may be prepared by the following methods:

Method A

By reacting a 2-phenylimino-imidazolidine of the general formula

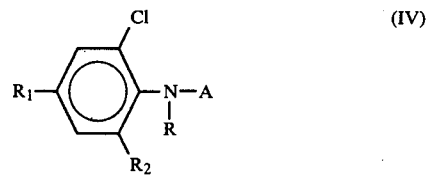
(II)

where $R_1$ and $R_2$ are as defined above for Formula I, with a halide of general formula Hal—R (III)

where Hal represents a chlorine, bromine, or iodine atom and R is as defined above.

Method B

By reacting a compound of the general formula

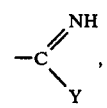
(IV)

where $R_1$, $R_2$, and R are as defined above and

A represents a cyano group or the group

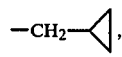

where Y is an alkoxy group having from 1 to 4 carbon atoms, an alkylthio group having from 1 to 4 carbon atoms, a sulfhydryl group or an amino group, with ethylenediamine or an acid addition salt thereof.

Certain compounds within the scope of Formula I, namely, 2-[N-Subst. phenyl)-N-(subst. methoxyamino]-2-imidazolines of the general formula

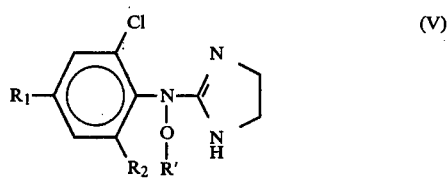
(V)

where $R_1$ and $R_2$ are as defined above for Formula I and R' represents a radical selected from the group consisting of $-CH_2-CH=CH_2$, $-CH_2-C(CH_3)=CH_2$, $-(CH_2)_2-CH=CH_2$, $-CH_2-CH=CH-CH_3$, and $-CH_2-\triangleleft$, are prepared by the following method:

Method C

By reacting a 2-[N-(subst. phenyl)-N-hydroxyamino]-2-imidazoline of the general formula

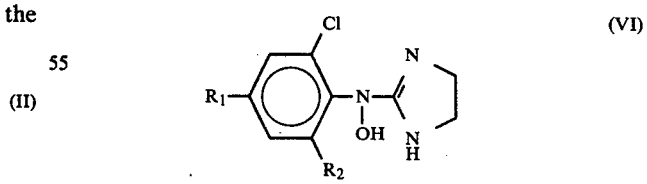
(VI)

wherein $R_1$ and $R_2$ are as defined above, is reacted with a halide of the general formula Hal—R' (VII)

wherein Hal and R' are as defined above.

In the alkylation of the -2-arylimino-imidazolidine of Formula II pursuant to Method A, the substitution is effected exclusively at the bridge nitrogen atom. In the reaction pursuant to Methods B and C, the structure of the end product is determined by the synthesis. The position of the substituent may also be determined by NMR-spectroscopy. [cf., H. Stähle et al., Liebigs Ann. Chem. 751, 159 et seq. (1971)].

It is advantageous to effect the reaction according to Methods A and C by heating the reaction partners, preferably in the presence of a polar or non-polar organic solvent, to temperatures of about 50° to 150° C. The specific reaction conditions depend to a great extent upon the reactivity of the reaction partners. It is recommended to provide the halide for the alkylation in excess and to perform the reaction in the presence of an acid-binding agent.

Method B is required to be performed at elevated temperatures between 60° and 180° C. Solvents are not necessary. It is advantageous to provide the ethylenediamine or its acid addition salt in excess.

The starting compounds of the Formula II are described, for example, in Belgian Pat. Nos. 623,305, 687,657, and 709,944, incorporated herein by reference.

The starting compounds of the Formulas III and VII may be prepared by halogenating the corresponding primary alcohol.

The compounds of the Formula IV are obtained, starting from anilines, by reaction with compounds of Formula III and subsequent reaction of the secondary amines formed thereby with cyanates or thiocyanates, whereby ureas or thioureas are formed. Ureas and thioureas may then be converted by alkylation agents into corresponding isouronium salts or isothiouronium salts. From these acid addition compounds the corresponding isoureas or isothioureas may be obtained with bases. By splitting off water from ureas or splitting off $H_2S$ from thioureas by means of lead or mercury salts, cyanamides are obtained which may be converted into guanidines by the addition of ammonia.

The starting compounds of Formula VI are obtained by oxidation of compounds of general Formula II with per acids corresponding to German Offenlegungsschrift No. 24 57 979, incorporated herein by reference.

The 2-phenylamino-2-imidazolines of Formula I are organic bases and therefore form acid addition salts with inorganic or organic acids. Examples of non-toxic, pharmacologically acceptable acid addition salts are those formed with, for example, hydrochloric acid, hydrobromic acid, hydriodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid p-aminobenzoic acid, phthalic acid, cinnamic acid, salicylic acid, ascorbinic acid, methanesulfonic acid, 8-chlorotheophylline, or the like.

The compounds of the present invention, that is, the compounds of Formula I above and their non-toxic, pharmacologically acceptable acid addition salts, have useful pharmacodynamic properties. More particularly, they exhibit very strong bradycardiac activity in warm-blooded animals, such as rabbits and rats, including spinal rats and intact, narcotized rats, and are therefore useful for the treatment of coronary diseases.

For pharmaceutical purposes the compounds of the present invention are administered to warm-blooded animals perorally or parenterally as active ingredients in customary dosage unit compositions, that is, compositions in dosage unit form consisting essentially of an inert pharmaceutical carrier, galenic excipient, disintegrant, lubricant, or substance for obtaining sustained release and one effective dosage unit of the active ingredient, such as tablets, coated pills, capsules, wafers, powders, solutions, suspensions, emulsions, syrups, suppositories, and the like. One effective dosage unit of the compounds according to the present invention is from 0.0017 to 1.33 mg/kg body weight, preferably 0.017 to 0.5 mg/kg body weight.

The following examples illustrate the present invention and will enable others skilled in the art to understand it more completely. It should be understood, however, that the invention is not limited solely to the particular examples given below.

EXAMPLE 1

2-[N-(2,6-dichlorophenyl)-N-(cyclopropylmethoxy)-amino]-2-imidazoline hydrobromide An amount of 6.0 gm (0.021 mol) of 2-[N-(2,6-dichlorophenyl)-N-hydroxyamino]-2-imidazoline hydrochloride was added to a solution of 0.93 gm of sodium in 95 ml of absolute ethanol. Then, 2.2 gm (117%), of chloromethylcyclopropane were added dropwise to the solution while stirring and the solution was refluxed for 30 minutes. The separated common salt was separated by suction filtration, and the mother liquor was evaporated to dryness in vacuo. The oil remaining in the brown colored residue was dissolved cold in dilute 1 N hydrochloric acid, and the solution was extracted with ether several times. The ethereal extracts were abandoned. After treatment with active charcoal, the hydrochloric acid solution was alkalized with 2 N sodium hydroxide solution, and the separated white substance was separated by suction filtration. The latter was pure, novel imidazoline base, i.e., 2-[N-(2,6-dichlorophenyl)-N-(cyclopropylmethoxy)mino]-2-imidazoline (as determined by thin-layer chromatography). The base was dissolved in a small amount of methanol and converted into hydrobromide salt by addition of conconcentrated hydrobromic acid. After addition of ether, the salt separates in crystalline form. Following suction filtration and drying, a yield of 1.1 gm (14.6% of theory) of the compound

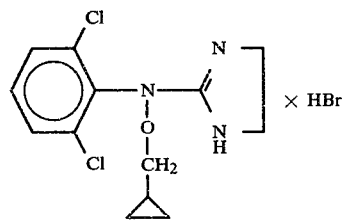

was obtained, m.p. 215°–216° C.

EXAMPLE 2

2-[N-(2,6-dichlorophenyl)-N-(2-methyl-1-butene-4-yl)-amino]2-imidazoline

A mixture of 6.9 gm (0.03 mol) of clonidine, 5.6 gm of 4-bromo-2-methyl-1-butene, and 5 ml of triethylamine in 25 ml of toluene was heated for 24 hours at 120° C. After cooling, the solvent was decanted, and the residue remaining was dissolved in 1 N hydrochloric acid. After extraction with ether several times (the ethereal extracts were abandoned), the solution was extracted with ether in fractions at stepwisely rising pH values (alkalizing with 2 N sodium hydroxide solution). The thin-layer chromatographically uniform ether extracts were united and dried over MgSO4, and the ether was evaporated in vacuo.

The yield was 1.8 gm (19.6% of theory) of the compound

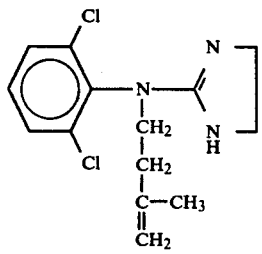

which had a melting point of 117°-119° C.

Using procedures analogous to those descirbed in Examples 1 and 2, the compounds of Formula I shown in the table below were also prepared. The melting points are those of the free bases, unless the salt form is otherwise indicated.

TABLE 1

| Example | R₁ | R₂ | R | M.p. (°C.) | Yield (% of theory) |
| --- | --- | --- | --- | --- | --- |
| 3 | H | Cl | —(CH₂)₂—CH=CH₂ | 133–135 | 39.6 |
| 4 | H | Cl | —O—CH₂—CH=CH₂ | 153–154 | 61.6 |
| 5 | H | Cl | —O—CH₂—C(CH₃)=CH₂ | 112–113 | 18.4 |
| 6 | H | Cl | —O—(CH₂)₂—CH=CH₂ | 108–109 | 39.6 |
| 7 | H | Cl | —O—CH₂—CH=CH—CH₃ | 135–138 | 47.6 |
| 8 | H | CH₃ | —(CH₂)₂—C(CH₃)=CH₂ | 109–111 | 19.3 |
| 9 | H | Cl | —CH₂—⟨C₆H₄⟩—OH | 261 (hydrobromide) | 90.4 |
| 10 | H | Cl | —CH₂—⟨C₆H₄⟩—OCH₃ | 118.5–119.5 | 63.6 |
| 11 | CH₃ | Cl | —CH₂—C₆F₅ | 225–227 (hydrobromide) | 32.6 |
| 12 | H | Cl | —CH₂—C₆F₅ | 228–231 (hydrobromide) | 43.3 |
| 13 | Cl | H | —CH₂—C₆F₅ | 181–184 (hydrochloride) | 27.4 |
| 14 | H | Cl | —CH₂—⟨C₆H₄⟩—F | 99–101 | 45.3 |
| 15 | H | Cl | —CH₂—CH=CH—C₆H₅ | 114–116 | 56.8 |
| 16 | H | Cl | —CH₂—C₆H₅ | 103–105 | 12.8 |
| 17 | H | CH₃ | —CH₂—CH=CH—C₆H₅ | 109–111 | 17.4 |

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 18

Coated tablets

The tablet, or pill, core composition can be compounded from the following ingredients:

| Component | Parts |
| --- | --- |
| Compound prepared in Example 1 | 5 |
| Lactose | 65 |
| Corn starch | 130 |
| Secondary calcium phosphate | 40 |
| Soluble starch | 3 |
| Magnesium stearate | 3 |
| Colloidal silicic acid | 4 |
| Total | 250 |

Preparation:

The active ingredient is admixed with a portion of the excipients, the mixture is thoroughly kneaded with an aqueous solution of the soluble starch, the moist mass is granulated through a screen, and the granulate is dried. The dry granulate is admixed with the remainder of the excipients, and the composition is compressed in 250 mg tablet cores which are subsequently coated with a thin shell consisting essentially of a mixture of sugar, talcum, and gum arabic. Each coated tablet is an oral dosage unit composition containing 5 mg of the active ingredient.

EXAMPLE 19

Hypodermic solution

The solution can be compounded from the following ingredients:

| Component | Amount |
|---|---|
| Compound prepared in Example 1 | 1.0 mg |
| Sodium chloride | 18.0 mg |
| Distilled water  q.s. ad | 2.0 ml |

Preparation:

The active ingredient and the sodium chloride are dissolved in the distilled water, the solution is filtered until free from suspended particles, and the filtrate is filled under aseptic conditions and in an atmosphere of nitrogen into 2 cc-ampules which are then sterilized and sealed. The contents of each ampule are an injectable dosage unit composition containing 1 mg of the active ingredient.

EXAMPLE 20

Drop solution

The solution can be compounded from the following ingredients:

| Component | Amount |
|---|---|
| Compound prepared in Example 1 | 0.02 gm |
| Methyl p-hydroxybenzoate | 0.07 gm |
| Propyl p-hydroxybenzoate | 0.03 gm |
| Demineralized water  q.s. ad | 100.0 ml |

Preparation:

The active ingredient and the p-hydroxy-benzoates are dissolved in the demineralized water, the solution is filtered, and the filtrate is filled in 100 ml-bottles equipped with a dropping spout. An amount of 10 cc of the solution is an oral dosage unit composition containing 2 mg of the active ingredient.

Any one of the other compounds embraced by Formula I or a non-toxic, pharmacologically acceptable acid addition salt thereof may be substituted for the particular active ingredient in Examples 18 through 20. Likewise, the amount of active ingredient in these illustrative examples may be varied to achieve the dosage unit range set forth above, and the amounts and mature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments and that various changes and modifications may be made without departing from the spirit of the invention or the scope of the appended claims.

We claim:

1. A compound of the formula

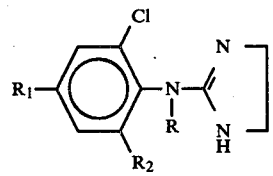

wherein
R$_1$ and R$_2$, which may be the same or different, represent a hydrogen atom, a chlorine atom, or a methyl group, with the proviso that not both R$_1$ and R$_2$ are hydrogen, and
R represents a radical selected from the group consisting of —(CH$_2$)$_2$—C(CH$_3$)=CH$_2$, —(CH$_2$)$_2$—CH=CH$_2$, —O—CH$_2$—CH=CH$_2$, —O—(CH$_2$)$_2$—CH=CH$_2$, —O—CH$_2$—C(CH$_3$)=CH$_2$, —O—CH$_2$—CH=CH—CH$_3$,

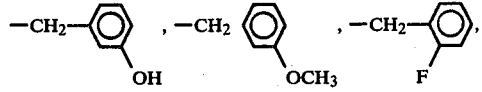

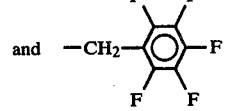

or a non-toxic, pharmacologically acceptable acid addition salt thereof.

2. A bradycardiac pharmaceutical dosage unit composition consisting essentially of an inert pharmaceutical carrier and an effective bradycardiac amount of a compound of claim 1.

3. The method of slowing the heart rate of a warm-blooded animal in need thereof, which comprises perorally or parenterally administering to said animal an effective bradycardiac amount of a compound of claim 1.

* * * * *

UNITED STATES PATENT AND TRADEMARK OFFICE
CERTIFICATE OF CORRECTION

PATENT NO. : 4,277,487
DATED : July 7, 1981                                    Page 1 of 2
INVENTOR(S) : HELMUT STÄHLE ET AL.

It is certified that error appears in the above—identified patent and that said Letters Patent is hereby corrected as shown below:

Preamble page, under [75]: "Helmut Stahle" should read -- Helmut Stähle --.

under [56]: "Stämle" should read -- Stähle --.

Abstract, line 9 after structural formula: "($CH_3$" should read -- ($CH_3$)- --.

Abstract, line 10 after structural formula: Delete ")".

Abstract, line 7 after structural formula; Column 1, line 30; Column 8, line 25:
"($CH_2$-" should read -- $(CH_2)_2$- --.

Abstract, line 8 after structural formula; Column 1, line 31; Column 8, line 26:
Delete ")$_2$-".

Column 1, line 32; Column 8, line 27:
"-O-CH-" should read -- -O-$CH_2$- --.

Column 1, line 33; Column 8, line 28: Delete "$_2$-"

UNITED STATES PATENT AND TRADEMARK OFFICE
CERTIFICATE OF CORRECTION

PATENT NO. : 4,277,487
DATED : July 7, 1981
INVENTOR(S) : HELMUT STÄHLE ET AL.

It is certified that error appears in the above—identified patent and that said Letters Patent is hereby corrected as shown below:

Column 1, Formula (II): The portion of the formula which reads

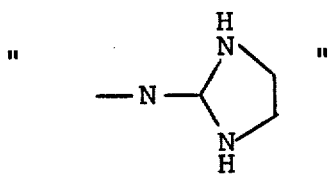  should read  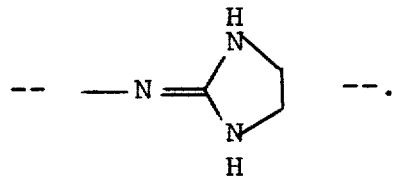.

Column 3, line 53: After "p-hydroxybenzoic acid" insert a comma -- , --.

Signed and Sealed this

Eighth Day of September 1981

[SEAL]

Attest:

Attesting Officer

GERALD J. MOSSINGHOFF

Commissioner of Patents and Trademarks